(12) United States Patent
Wolf, Jr. et al.

(10) Patent No.: US 6,635,324 B1
(45) Date of Patent: Oct. 21, 2003

(54) MEDICAL GRADE TUBING AND METHODS FOR COUPLING SAME

(75) Inventors: Ludwig Wolf, Jr., Barrington, IL (US); Michael T. K. Ling, Vernon Hills, IL (US)

(73) Assignee: Baxter International, Inc., Round Lake, IL (US)

( * ) Notice: Subject to any disclaimer, the term of this patent is extended or adjusted under 35 U.S.C. 154(b) by 0 days.

(21) Appl. No.: 09/009,969

(22) Filed: Jan. 21, 1998

(51) Int. Cl.[7] .......................... A61M 25/00; B32B 7/02; C08L 23/06
(52) U.S. Cl. ................ 428/36.9; 428/35.3; 428/476.1; 428/515; 428/516; 428/518; 428/519; 428/520; 428/522; 604/96; 604/264; 604/265; 604/270; 604/280; 604/282
(58) Field of Search ........................... 428/35.3, 36.9, 428/516, 518, 520, 476.1

(56) References Cited

U.S. PATENT DOCUMENTS

| | | | | |
|---|---|---|---|---|
| 4,950,347 A | * | 8/1990 | Futagawa ................. 156/272.4 |
| 5,645,904 A | * | 7/1997 | Woo et al. ................. 428/35.7 |
| 5,681,627 A | * | 10/1997 | Mueller ..................... 428/35.3 |
| 5,686,527 A | * | 11/1997 | Laurin et al. .................. 525/66 |
| 5,730,919 A | * | 3/1998 | Wilfong et al. ......... 264/173.11 |
| 5,741,452 A | * | 4/1998 | Ryan et al. ............... 264/209.5 |
| 5,766,744 A | * | 6/1998 | Fanselow et al. ........... 428/213 |
| 5,773,155 A | * | 6/1998 | Kale ........................... 428/523 |
| 5,846,620 A | * | 12/1998 | Compton ................... 428/35.7 |
| 5,932,307 A | * | 8/1999 | Ryan et al. ................ 428/36.9 |

FOREIGN PATENT DOCUMENTS

| | | | | |
|---|---|---|---|---|
| WO | WO 93/15908 | * | 8/1993 | ........... B32B/27/08 |
| WO | WO97/42020 | | 11/1997 | |
| WO | WO98/00286 | | 1/1998 | |

OTHER PUBLICATIONS

Webster's Seventh New Collegiate Dictionary, (1972), pp. 390 and 705.*
"Sterile, Safe, Strong Tubing Connections," Brochure from Baxter Healthcare Corporation, Biotech North America, 1995, 2 pages.

* cited by examiner

Primary Examiner—Sandra M. Nolan

(57) ABSTRACT

A medical grade tubing that includes a layer of ultra low density polyethylene that has been let down, or drawn down, in diameter approximately 10% to about 50% in an extrusion process and an inner layer of an RF responsive material, the tubing allowing for the selective connection of the tubing to another tubing using a sterile welding device.

17 Claims, 2 Drawing Sheets

MEDICAL GRADE TUBING AND METHODS FOR COUPLING SAME

BACKGROUND OF THE INVENTION

The present invention relates generally to medical products. More specifically, the present invention relates to medical grade tubing and methods of connecting same in a sterile manner.

It is of course known to house medical products in containers. It is likewise known to store certain medical products, e.g., blood and blood components, in containers. It is likewise known to use tubing to: access the containers; allow for the mixing of products; and/or infuse the products into a patient. For example, it is known to collect blood products from a patient and store same in flexible plastic containers. It is also known to treat these medical products, e.g., centrifuge the blood, and combine the resultant product with other components. These products can then be infused into a patient.

In order to allow one to access the container containing a medical product or fluid, either to further treat the product, combine it with another product, add a product to the container, or infuse the product into a patient, it is known to use flexible tubes. These tubes must be made from medical grade plastics, e.g., a plastic that is inert and will not contaminate the medical product so that it can be infused or used with a patient. For example, it is known to use polyvinyl chloride (PVC) to manufacture such tubing.

At various times it may be desirable to connect one or more tubes together. Such connections preferably are made using a sterile process; otherwise, after the connection is made, it is necessary to re-sterilize the two tubes that have been connected.

Thus, sterile connection devices have been developed. One such device is available from Baxter Healthcare Corporation, Biotech North America, Deerfield, Ill. under the name "SCD® 312 Sterile Tubing Welder." This connection device allows two tubes to be sterilely connected together. Briefly, the device utilizes a wafer (sealing head), that is heated to more than 500° F. The wafer welds two separate tubing segments together. Due to the process used, contaminants are destroyed at the welding site providing a new connection that is strong enough to withstand the rigors that the product may be subject to, for example, with respect to a blood collection device- blood processing, infusing and collecting.

In the blood collection arena, such a connection device can be used to: add leukocyte filters to red cell units; pool blood products and prepare blood components using blood transfer packs; attach a sterile dock set to apheresis platelets collected with a blood cell separator; prepare aliquots for pediatric use; add different needles to sets; and other process, sample and related connection without comprising the products sterility or dating.

Although the SCD® 312 Sterile Tubing Welder provides a sterile, safe, and efficient method of connecting tubes, due to its effectiveness any polyvinyl chloride tubing can be connected to any other tubing of comparable size. This may create potential issues in that any tube, even those tubes that are coupled to products that should be not be connected to other products due to an incompatibility of the products, can be erroneously or improperly connected.

Therefore, there is a need for an improved tubing that allows for the selective connection of a tubing to another tubing in a sterile connection device.

SUMMARY OF THE INVENTION

The present invention provides tubing, and methods of connecting tubing, that allows for the connection of the tubing to similar tubes in a sterile connection device, but, does not allow the tubing to be connected to a polyvinyl chloride tubing. Thus, the tubing allows for the selective sterile connection of the tubing to only select other tubing. This therefore prevents the tubing from being connected to a polyvinyl chloride tubing preventing the connection of incompatible products or devices.

To this end, the present invention provides a medical grade tubing comprising a layer of ultra low density polyethylene that has been let down, or drawn down, in diameter approximately 10% to about 50% in an extrusion process and an inner layer of an RF active material.

In an embodiment, the tubing includes an outer layer of a polyvinyl chloride material.

In an embodiment, the ultra low density polyethylene is let down 50% in the extrusion process.

In an embodiment, the inner layer is chosen from the group consisting of ethylene vinyl acetate, polyamide alloy, and polyvinyl chloride.

In an embodiment, the tubing is co-extruded.

In an embodiment, the inner layer has a thickness of approximately 0.001 inches to about 0.010 inches, the core layer has a thickness of approximately 0.008 inches to about 0.020 inches, and the outer layer has a thickness of approximately 0.001 inches to about 0.005 inches.

In another embodiment of the invention, two medical grade tubes are provided. The tubings have been coupled together in a sterile connection device and comprising a first tubing having a core layer of ultra low density polyethylene that has been let down, or drawn down, in diameter 10% to about 50% in an extrusion process, an inner layer of an RF active material, and an outer layer of a polyvinyl chloride material, and a second tubing that does not include polyvinyl chloride.

In an embodiment, the first tubing includes an outer layer of polyvinyl chloride.

In a still further embodiment, a method for allowing for the selective sterile connection of medical grade tubing is provided comprising a first tubing comprising a core layer of ultra low density polyethylene that has been let down, or drawn down, in diameter approximately 10% to about 50% in an extrusion process and an inner layer of an RF active material, the first tube being so constructed and arranged that it can not be sterile connected to a polyvinyl chloride tubing using a sterile connection device including a heat sealing device.

An advantage of the present invention is that it allows for the selective connection of two tubes.

Still, an advantage of the present invention is that it provides proprietary tubing that cannot be connected to a standard polyvinyl chloride tubing.

Moreover, an advantage of the present invention is that it provides an improved method for connecting at least certain tubes and preventing the connection of standard PVC tubing.

Furthermore, an advantage of the present invention is that is provides an improved tubing for use in a sterile connection device.

Additional features and advantages of the present invention are described in, and will be apparent from, the Detailed Description of the Presently Preferred Embodiments and from the drawings.

DETAILED DESCRIPTION OF THE PRESENTLY PREFERRED EMBODIMENTS

The present invention relates to medical grade tubing and methods of securing same. As noted in the background of the invention, for a variety of reasons it may be necessary to connect two separate medical grade tubes to each other. As is also noted in the background of the invention, such a connection preferably should be done in a sterile manner. Such a connection may be desirable to add a device, such as a needle onto another tubing, connect two products, or allow the infusion of a product into a patient or a device.

Figure 1A:
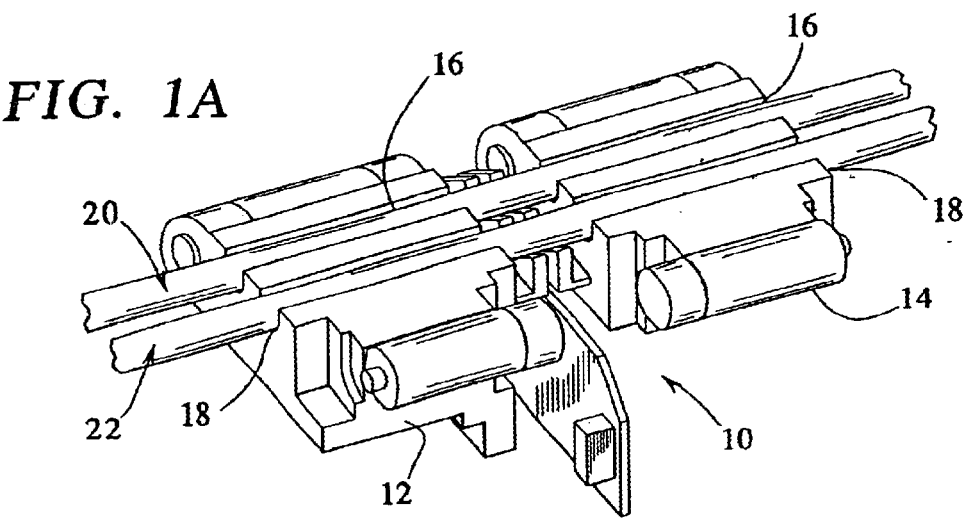
FIGS. 1A–1C illustrate schematically a connection device for connecting two tubes in a sterile manner.
Figure 1B:
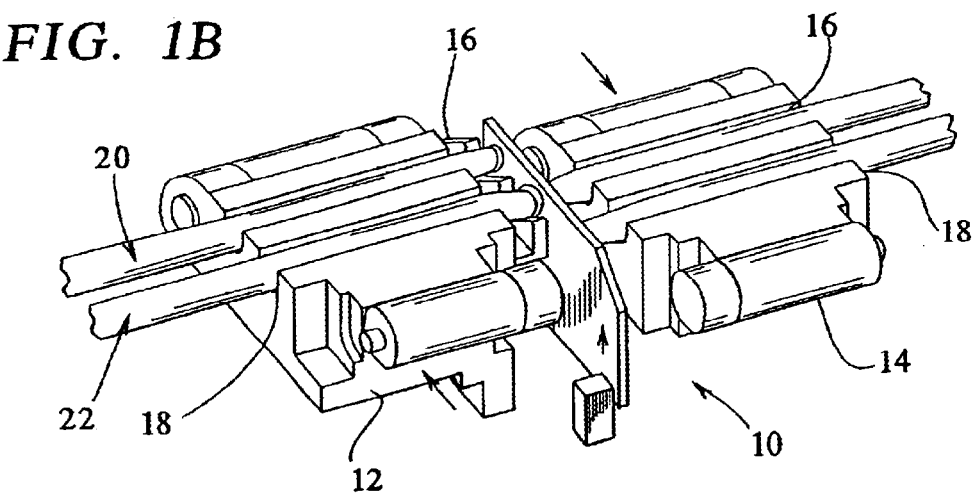
Figure 1C:
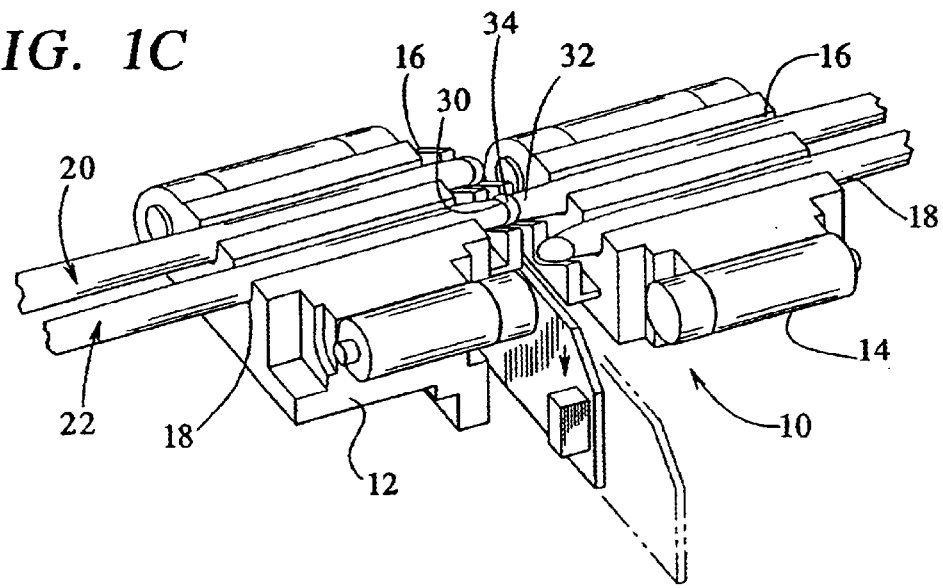

Referring generally to FIGS. 1A–1C, a device 10 for the sterile connection of two tubes is illustrated. As illustrated, generally the device 10 includes two members 12 and 14, each including a channel 16 and 18 for holding a tube 20 and 22 respectively. As illustrated in FIG. 1B, the members 12 and 14 can be moved in a parallel direction, opposite to each other.

Accordingly, as illustrated in FIG. 1A, tubes 20 and 22 are placed in each of the channels 16 and 18. A welding head 24 is then urged upwardly against and through the tubes 20 and 22. The welding head is heated to a temperature of approximately 500° F. Thus, the welding head thereby welds and separates the two tubes 20 and 22.

At the same time that the welding head 24 passes through the tubes 20 and 22, the tubes are shifted because the channels 16 and 18 containing the tubings are moved in opposite directions. The welding head 24 is then lowered as a first end 30 of the second tube 22 is urged against a second end 32 of the first tube 20. This thus seals the two tubes together at a sterile connection 34. Such a device is commercially available from Baxter Healthcare Corporation, Biotech North America, Deerfield, Ill., under the name SCD® 312 Sterile Tubing Welder.

The tubing of the present invention is designed to selectively allow sterile connections using devices such as those set forth in FIG. 1 including, but not limited to, the SCD® 312 Sterile Tubing Welder.

Perhaps, the most commonly used medical grade tubing is polyvinyl chloride. Most medical grade tubing can be sterilely connected to polyvinyl chloride using a device such as that set forth in FIG. 1. Unfortunately a problem that can arise using a device 10 such as that illustrated in FIG. 1, is that the sterile connection device 10 allows any PVC tubing to be connected to any other PVC tubing. Thus, even though a manufacturer of the product may not want certain products, and thereby certain tubing, connected to another product (tubing), because the devices or products to which the tubing is connected are incompatible, a sterile connection device would allow same to be coupled together.

Pursuant to the present invention, tubing is provided that cannot be connected to polyvinyl chloride tubing using a sterile connection device or system. Instead, the tubing can only be connected to similar tubing in a device such as that illustrated in FIG. 1. Thus, the tubing of the present invention allows the manufacturer to provide products that can only be coupled to each other and not inappropriately or inadvertently coupled to incompatible devices or products.

Figure 2:
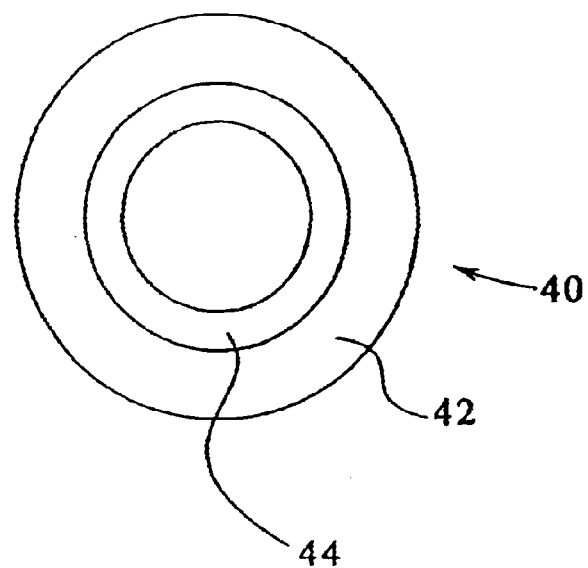
FIG. 2 illustrates a cross-sectional perspective view of an embodiment of the present invention.

Referring to FIG. 2, an embodiment of the tubing 40 of the present invention is illustrated in cross-section. In the preferred embodiment the tubing 40 is co-extruded. The tubing 40 includes a first layer 42 of ultra low density polyethylene that has been let down, or drawn down, in diameter approximately 10 to about 50% in an extrusion process. In a preferred embodiment, the ultra low density polyethylene has been let down, or drawn down, in diameter 50% in the extrusion process. As used herein, a 50% let down, or drawn down, in diameter in an extrusion process means that the tubing was extruded with a much larger bushing such that during extrusion the tubing diameter was reduced to 50% of the bushing by means of take up. This thereby stretches the tubing by 50%. Ultra low density polyethylene is available from Dow Chemical Company, Exxon, and Mitsui Chemkal.

Because ultra low density polyethylene is not a dielectric responsive material, and therefore cannot be RF welded, the tubing includes a second layer 44. This second layer 44 is an RF active layer. The second layer 44 can be any material selected from the group consisting of ethylene, vinyl acetate, polyamide alloy, or polyvinyl chloride. This layer is co-extruded onto the inner surface 42 of the tubing 40. Thus, the resultant tubing 40 can be RF heat sealed.

Preferably the tubing 40 has a cross-sectional thickness of approximately 0.018 inches to about 0.022 inches with the thickness of the inner layer 42 being approximately 0.001 inches to about 0.010 inches and the thickness of the outer layer 44 being approximately 0.008 inches to about 0.020 inches.

Figure 3:
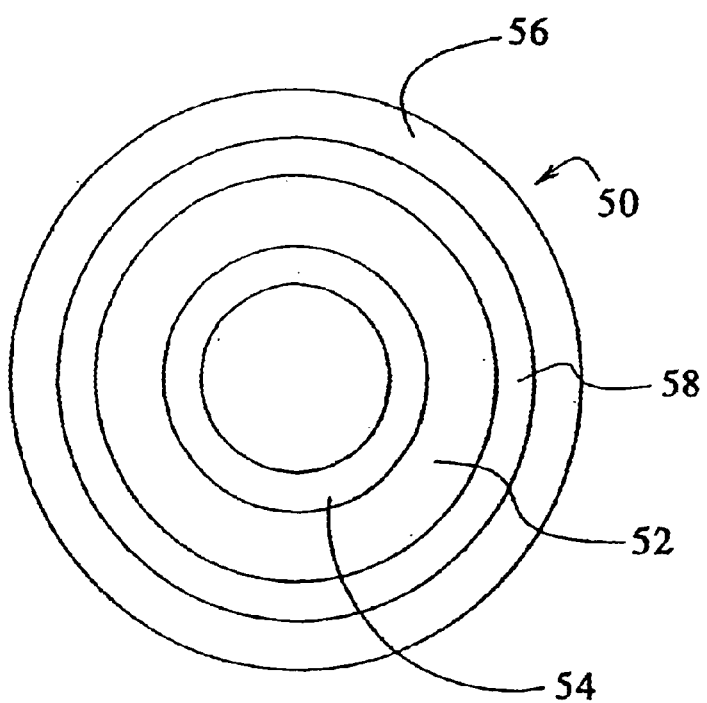
FIG. 3 illustrates a cross-sectional perspective view of another embodiment of the present invention.

Referring to FIG. 3., a further embodiment of the invention is illustrated wherein the tubing 50 includes a third layer 56 of polyvinyl chloride. To this end, the first layer 52 is a layer of ultra low density polyethylene let dawn; or drawn down, in diameter approximately 10 to about 50% and most preferably 50% in the extrusion process. The second layer 54 is an RF responsive material chosen from the group consisting of ethylene vinyl acetate, polyamide alloy, and polyvinyl chloride. As previously noted, the third layer 56 is constructed from polyvinyl chloride and is co-extruded to the outer surface of the tubing using a tie layer 58 such as acid modified ethylene vinyl acetate.

Preferably the tubing 50 has a cross-sectional thickness of approximately 0.018 inches to about 0.022 inches with the thickness of the inner layer 52 being approximately 0.001 inches to about 0.010 inches, the thickness of the outer layer being approximately 0.001 inches to about 0.005 inches, and the thickness of the middle layer is approximately 0.008 inches to about 0.020 inches.

An advantage of the tubing 50 is that although it cannot be sealed to a PVC tubing using a sterile connection device, such as 10 of FIG. 1, it can be solvent bonded to a PVC part if needed due to the PVC layer 56.

Each of the tubes 40 and 50 of the present invention can be sealed to each other using a sterile connection system such as that illustrated in FIG. 1. However, these tubes 40 and 50 cannot be sealed to a polyvinyl chloride tubing using such a device. In this regard, if one attempts to use to seal the tubing 40 and 50 of the present invention to a polyvinyl chloride tubing using the device 10 of FIG. 1, the seal will separate. This will prevent the tubes 40 and 50 from being sealed to a PVC tube. Thus, although the tubes of the present invention can be sterile welded to each other; they however cannot be sterile welded to polyvinyl chloride tubing.

It should also be noted that the tubes 40 and 50 can be RF heat sealed.

By way of example and not limitation, examples of the present invention will now be given.

Tubing was extruded from the following plastic materials other than polyvinyl chloride: various ethylene vinyl acetates and various ultra low density polyethylenes.

Each of the tubes was attempted to be sterile connected to each other using the SCD® 312 Sterile Tubing Welder. All of the preceding materials passed the test.

After each of the tubes was welded to itself an attempt was made to pop open the seal of the tubing. It was found that only tubing made from Dow Chemical VP8770 ultra low density polyethylene material passed this test.

Then an attempt was made to weld the tubing to a standard polyvinyl chloride tubing. The ultra low density polyethylene tubing would not weld to the polyvinyl chloride tubing.

It should be understood that various changes and modifications to the Presently Preferred Embodiments described herein will be apparent to those skilled in the art. Such changes and modifications can be made without departing from the spirit and scope of the present invention and without diminishing its attendant advantages. It is therefore intended that such changes and modifications be covered by the appended claims.

We claim:

1. A medical grade tubing comprising:

a layer of a non RF responsive material comprising ultra low density polyethylene that has been let down, or drawn down, in diameter approximately 10% to about 50% in an extrusion process; and an inner layer of an RF responsive material.

2. The medical grade tubing of claim 1 including an outer layer of polyvinyl chloride.

3. The medical grade tubing of claim 1 wherein the ultra low density polyethylene is let down, or drawn down, in diameter 50% in the extrusion process.

4. The medical grade tubing of claim 1 wherein the inner layer is chosen from the group consisting of ethylene vinyl acetate, polyamide alloy, and polyvinyl chloride.

5. The medical grade tubing of claim 1 wherein the tubing is co-extruded.

6. The medical grade tubing of claim 1 wherein:

the inner layer has a thickness of approximately 0.001 inches to about 0.010 inches; and a core layer has a thickness of approximately 0.008 inches to about 0.020 inches.

7. The medical grade tubing of claim 2 wherein the outer layer has a thickness of approximately 0.001 inches to about 0.005 inches.

8. The medical grade tubing of claim 1 wherein the tubing can be RF heat sealed.

9. The medical grade tubing of claim 1 wherein the tubing can be solvent bonded to a polyvinyl chloride tubing.

10. Two medical grade tubes that are coupled together using a sterile connection process comprising:

a first tubing having a non RF responsive layer of ultra low density polyethylene that has been let down, or drawn down, in diameter approximately 10% to about 50% in an extrusion process, and an inner layer of an RF responsive material; and a second tubing that does not include polyvinyl chloride.

11. The two medical grade tubes of claim 10 wherein the first tubing includes an outer layer of polyvinyl chloride material.

12. The two medical grade tubes of claim 10 wherein the ultra low density polyethylene is let down, or drawn down, in diameter 50% in the extrusion process.

13. The two medical grade tubes of claim 10 wherein the inner layer of the first tubing is chosen from the group consisting of ethylene vinyl acetate, polyamide alloy, and polyvinyl chloride.

14. The two medical grade tubes of claim 10 wherein the first tubing is co-extruded.

15. The two medical grade tubings of claim 11 wherein:

the inner layer of the first tubing has a thickness of approximately 0.001 inches to about 0.010 inches;

the core layer of the first tubing has a thickness of approximately 0.008 inches to about 0.020 inches; and the outer layer of the first tubing has a thickness of approximately 0.001 inches to about 0.004 inches.

16. A method for the selective sterile connection of medical grade tubing comprising:

providing a first medical grade tubing comprising a non RF responsive core layer of ultra low density polyethylene that has been let down, or drawn down, in diameter 10% to about 50% in an extrusion process and an inner layer of an RF responsive material, the first tubing being so constructed and arranged that it can not be sterile connected to a polyvinyl chloride tubing using a welding device; and connecting the medical grade tubing to another medical grade tubing using a welding device.

17. The method of claim 16 wherein the tubing includes an outer layer of a polyvinyl chloride material.

* * * * *